(12) United States Patent
Zhang et al.

(10) Patent No.: US 8,992,082 B2
(45) Date of Patent: Mar. 31, 2015

(54) G-ARM X-RAY IMAGING APPARATUS

(71) Applicants: Jun Zhang, Needham, MA (US); Liu Cao, Needham, MA (US); Shiyu Wei, Needham, MA (US); Sean Zhu, Needham, MA (US)

(72) Inventors: Jun Zhang, Needham, MA (US); Liu Cao, Needham, MA (US); Shiyu Wei, Needham, MA (US); Sean Zhu, Needham, MA (US)

( * ) Notice: Subject to any disclaimer, the term of this patent is extended or adjusted under 35 U.S.C. 154(b) by 52 days.

(21) Appl. No.: 13/953,776

(22) Filed: Jul. 30, 2013

(65) Prior Publication Data

US 2015/0036799 A1 Feb. 5, 2015

(51) Int. Cl.
*H05G 1/02* (2006.01)
*A61B 6/00* (2006.01)

(52) U.S. Cl.
CPC .................... *A61B 6/4429* (2013.01)
USPC ........................................ 378/197

(58) Field of Classification Search
CPC ...... H05G 1/02; A61B 6/4441; A61B 6/4405; A61B 6/4429
USPC ................................. 378/193–198
See application file for complete search history.

(56) References Cited

U.S. PATENT DOCUMENTS

| | | |
|---|---|---|
| 3,549,885 A | 12/1970 | Joenkoeping et al. |
| 4,884,293 A | 11/1989 | Koyama |
| 5,095,501 A | 3/1992 | Kobayashi |
| 5,515,416 A | 5/1996 | Siczek et al. |
| 5,923,721 A | 7/1999 | Duschka |
| 6,104,780 A | 8/2000 | Hanover et al. |
| 6,113,264 A | 9/2000 | Watanabe |
| 6,364,526 B2 | 4/2002 | Ivan et al. |
| 6,789,941 B1 | 9/2004 | Grady |
| 7,594,751 B2 | 9/2009 | Grebner et al. |

*Primary Examiner* — Courtney Thomas
(74) *Attorney, Agent, or Firm* — David J. Connaughton, Jr.; Gary E. Lambert; Lambert & Associates

(57) ABSTRACT

An X-ray imaging apparatus is provided having advantages of both C-shaped, G-shaped, and ring-shaped arm configurations. The device consists of a gantry that supports X-ray imaging machinery. The gantry is formed to allow two bi-planar X-rays to be taken simultaneously or without movement of the equipment and/or patient. The gantry is adjustable to change angles of the X-ray imaging machinery. Further, in some embodiments, the X-ray receptor portion of the X-ray imaging machinery may be positioned on retractable and extendable arms, allowing the apparatus to have a larger access opening when not in operation, but to still provide bi-planar X-ray ability when in operation.

20 Claims, 8 Drawing Sheets

G-ARM X-RAY IMAGING APPARATUS

BACKGROUND OF THE INVENTION

1. Field of the Invention

The present invention relates generally to a G-arm X-ray imaging apparatus. More particularly, the present invention relates to a G-arm X-ray imaging apparatus having a C-arm base having bi-planar imaging chains that may be side mounted or centrally mounted.

2. Description of Related Art

It is often desirable to take X-rays of a patient from a number of different positions, preferably without the need for frequent repositioning of the patient. It is preferable that the X-ray apparatus not unduly encumber the space surrounding the patient to enable a physician to treat or otherwise attend to the patient without the need to repeatedly remove and replace the X-ray apparatus. C-arm X-ray equipments has been developed to meet these needs and have become well known in medical art of surgical and other interventional procedures. An example of prior art C-arm equipment is shown in FIG. 1.

C-arm X-ray equipment is smart and flexible in operation, and in its positioning process, which can be reflected from the equipment's number of degrees of freedom of movement. The C-arm gantry is usually mounted so as to enable rotational movement of the arm in two degrees of freedom. Firstly, the C-arm gantry is slidably mounted to the support structure to enable orbiting rotational movement of the C-arm about its center of curvature (Direction marked 'A' in FIG. 1). Secondly, the C-arm equipment provides lateral rotation which is a motion rotating along the horizontal axis (Direction B in FIG. 1). In addition, the C-arm equipment also has a up-down motion along the vertical axis (Direction C in FIG. 1), a cross-arm motion along the horizontal axis (Direction D in FIG. 1) and a wig-wag motion along the vertical axis (Direction E in FIG. 1)

Although the C-arm X-ray equipment is smart and flexible in positioning process, it is often desirable to take X-rays of a patient from both the AP & LAT positions (two perpendicular angles), in such situations, the operators have to reposition the C-arm because C-arm configurations do not allow for such perpendicular bi-planar imaging.

For taking the X-rays from different angles at the same time without repositioning the X-ray apparatus, such a configuration is often referred to as bi-planar imaging that allows an object to be viewed in two planes simultaneously. The two X-ray beams emitted from the two X-ray tubes may cross at an iso-center.

Bi-planar imaging may be accomplished in several ways. One way is by using two independent imaging systems, such as two C-arms. U.S. Pat. No. 4,884,293 issued Nov. 28, 1989, to Koyama discloses a dual imaging system with one imaging system being mounted to the floor and the other being mounted to the ceiling. One disadvantage of this system is that, although the C-arms are coordinated, the imaging systems operate independently of one another. Thus the images produced are not coordinated. Another disadvantage of this configuration is that the two C-arms occupy too much space, inconveniencing the operators.

Another configuration for bi-planar imaging is mounting two imaging chains in a ring. U.S. Pat. No. 3,549,885 issued Dec. 22, 1970, to Andersson discloses a dual imaging system with both imaging systems being mounted perpendicularly in a rotatable ring. One disadvantage of the system compared to C-arm system is that the imaging chain only has the orbital rotation ability, but no lateral rotation ability (can be rotated along the ring only).

Another configuration for bi-planar imaging is mounting the two imaging chains onto a G-arm. U.S. Pat. No. 5,095,501 issued Mar. 10, 1992, to Kobayashi discloses a dual imaging system with both imaging systems being mounted perpendicularly in a G-arm gantry. The configuration can get the photos of two perpendicular positions at the same time. While the two imaging system are mounted on the inner circumference of the G-arm gantry, at one aspect larger orbital rotation angle is obtained, but on the other aspect, as we know, the inner space of the gantry is important to both the patient and the operator, so one disadvantage of this configuration is that there is not enough operation space, especially compared to the C-arm configuration.

Another configuration for bi-planar imaging is disposed two C-arm at one base. U.S. Pat. No. 6,104,780 issued Aug. 15, 2000, to Barry Hanover discloses a bi-plane imaging system with the first C-arm is large and disposed on a wheeled base while the second C-arm is smaller and disposed on the first C-arm such that it nests. As with other configurations, the disadvantage is that the operation space is limited because of the two nested C-arms.

SUMMARY OF THE INVENTION

The subject matter of this application may involve, in some cases, interrelated products, alternative solutions to a particular problem, and/or a plurality of different uses of a single system or article.

It is an object of the present invention to provide two side-mounted perpendicular imaging chains.

In one embodiment, the C-arm equipment is smart and flexible, which should be attributed to the C-arm base. The C-arm base could be a floor-mounted one, a ceiling mounted one, and/or a wheeled mobile one. The common feature is that the C-arm base can provide at least the orbital rotation and the lateral rotation. Other motion degrees of freedom can also be provided. Mounting G-arm gantry and imaging chains to a C-arm base would make the G-arm equipment smarter and more flexible. G-arm equipment could have both the orbital rotation and the lateral rotation like a C-arm.

In another embodiment, two side-mounted imaging chains are introduced to the G-arm equipment. Each imaging chain contains at least one X-ray source and one receptor mounted on the opposing ends of the G-arm gantry. One imaging chain is perpendicular to another. The advantage of the perpendicular imaging chain is that radiography or fluoroscopy can be performed at both the AP&LAT positions simultaneously without repositioning the equipment. The advantage of the side-mounted imaging chain is that a greater orbital rotation angle can be obtained, without loss of patient or operation space, because the imaging chain elements do not get in the way of the rotating gantry. In this embodiment, the orbital rotation angle could be larger than the existing G-arm and C-arm equipment.

In one aspect, a bi-planar X-ray apparatus is provided. The apparatus has a support gantry, with two X-ray imaging chains attached to it. The first and second imaging chains each comprise an X-ray source, an X-ray receptor, and a collimator. The two X-ray receptors are each connected to an arm, and each arm is adjustably mounted to the support gantry. The adjustable arms allow each of the X-ray receptors to be moved between an extended position away from the gantry, to a retracted position close to the gantry. This aspect allows the X-ray apparatus, when the X-ray receptors are in an extended position to create a G-arm gantry having the bi-planar functionality and other advantages of G-arm X-ray apparatuses. Further, when the X-ray receptors of the apparatus are in a retracted position, the apparatus can operate with C-arm convenience with respect to adjustments, operation, positioning, and the like.

DETAILED DESCRIPTION

Figure 1:
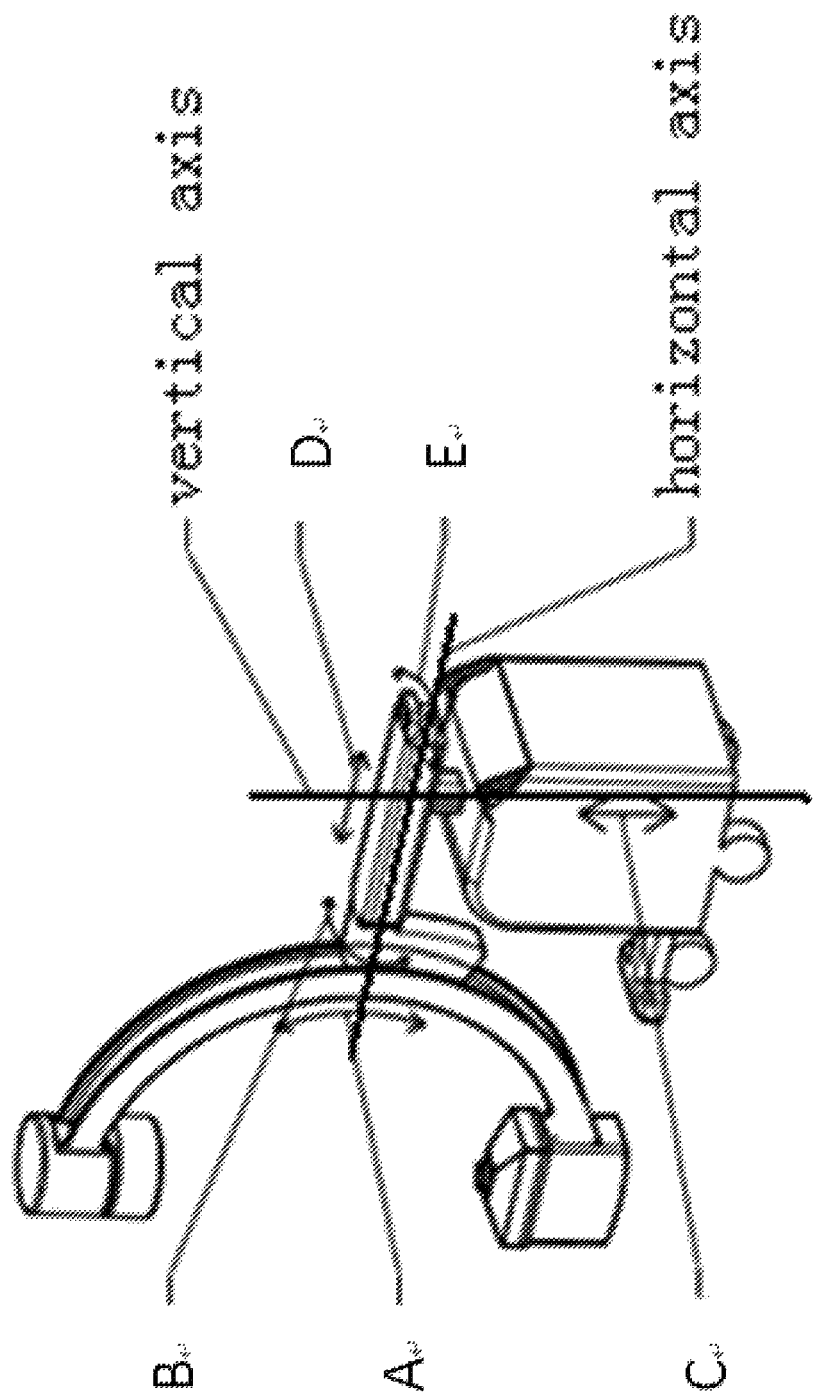
FIG. 1 provides an example of the structure of a general C-arm as known in the prior art, and the degrees of freedom of movement are specified.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

The need exists to develop a kind of bi-planar X-ray imaging apparatus with two X-ray imaging machinery formed as imaging chains, with both orbital and lateral rotation, and with a largest possible operating space. In one embodiment, the imaging chains are capable of perpendicular imaging. Meanwhile, the system should be more convenient for positioning and operation.

Generally, the present invention concerns an X-ray imaging apparatus having advantages of both C-shaped, G-shaped and ring-shaped arm configurations. The device consists of a gantry that supports X-ray imaging machinery. The gantry is formed to allow two bi-planar X-rays to be taken simultaneously or without movement of the apparatus and/or without movement of a patient being examined. The gantry is adjustable along a plurality of degrees of freedom of movement to change angles of the X-ray imaging machinery. Further, in some embodiments, an X-ray receptor portion of the X-ray imaging machinery may be positioned on retractable and extendable arms, allowing the apparatus to have a larger access opening when not in operation, but to still provide bi-planar X-ray ability when in operation. In alternative embodiments, the X-ray receptors may be rotated into position on rotatable arms, or otherwise brought from an extended to retracted position.

Generally, the gantry is arced in shape, however the gantry may be any shape allowing it to provide bi-planar X-ray imaging.

In addition to adjustment of the gantry supporting the X-ray imaging machinery, the gantry may be mounted to a base in such a way that allows for any number of motions, such as forward-back, left-right, up-down, axial motions, rotations, and the like. Further, in one embodiment, the base may be wheeled or otherwise portable, allowing the apparatus to be transported from one site to another.

In varying embodiments, a computerized control system may be implemented to enhance the functionality and ease of use of the X-ray imaging apparatus. The computerized control system may be in communication with the first and second imaging chains. Further, the computerized control system may be capable of controlling the operation of each of the imaging chains. For example, the computerized control system may be capable of operating the imaging chains simultaneously, or individually.

In other embodiments, a display may be integrated into the X-ray imaging apparatus to allow display or stored and/or recently recorded X-ray images. These images may be stored on the computerized control system and, by connecting the display with the computerized control system, easily displayed using the display.

Figure 2:
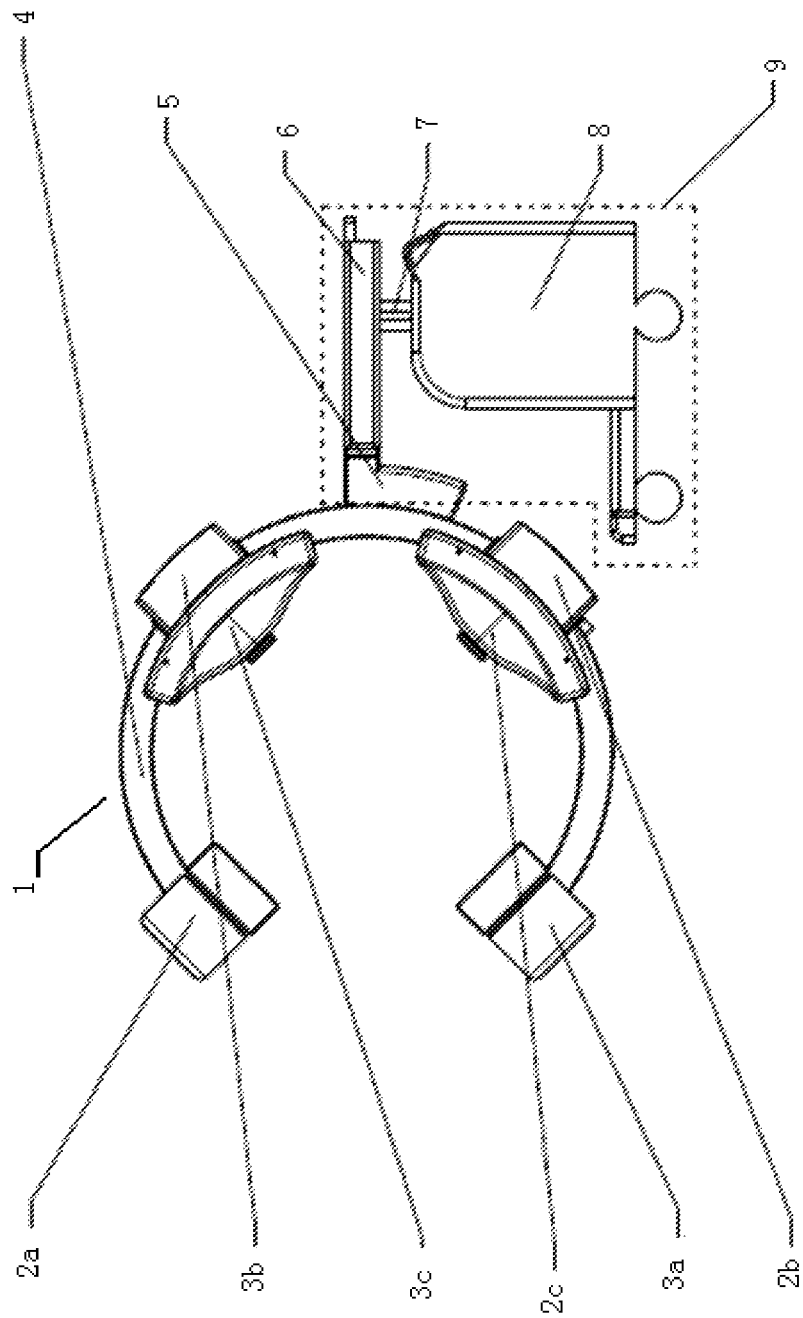
FIG. 2 provides a side view of the G-arm apparatus with two perpendicular image chains, which are side-mounted on a G-arm gantry, and with a C-arm base.

One embodiment of the present invention is illustrated in FIG. 2 wherein is shown a G-arm X-ray imaging apparatus is shown, generally designated at 1. The apparatus 1 comprises first receptor $2a$, first X-ray source $2b$, first collimator $2c$, second receptor $3a$, second X-ray source $3b$, second collimator $3c$, G-arm gantry 4, gantry support 5, cross arm 6, up-down column 7, and wheeled cart 8. Base 9 is composed by 5, 6, 7 and 8. Elements $2a$, $2b$ and $2c$ compose the first imaging chain of the X-ray imaging machinery. Elements $3a$, $3b$ and $3c$ compose the second imaging chain of the X-ray imaging machinery. The first and second image receptors $2a$, $3a$ may be any image receptor, such as an image intensifier, a flat panel detector, or the like.

The wheeled cart 8 enables transport of the G-arm apparatus 1 from one place to another. It is often highly advantageous to be able to move the G-arm apparatus 1 from one room to another conveniently, increasing the access by patients in many different rooms of a hospital.

Figure 3:
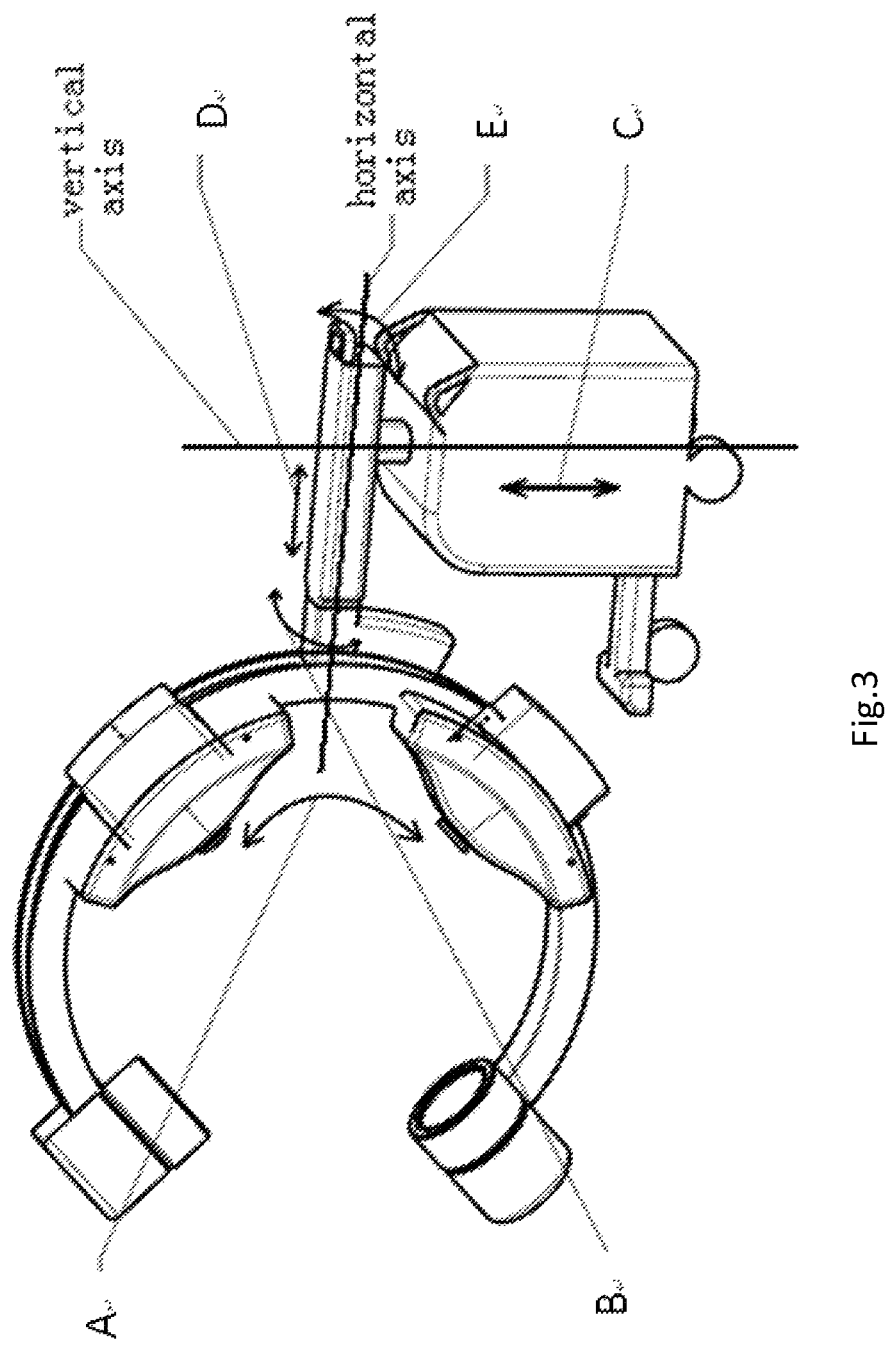
FIG. 3 provides a perspective view of an embodiment of the apparatus focusing on the degrees of freedom of movement of the X-ray apparatus in this invention.

As illustrated in FIG. 2, the up-down column 7 is mounted on the wheeled cart 8. Two functions may be provided by the up-down column 7. One is that the up-down column 7 is used for lifting or pulling down the G-arm shown in FIG. 3 as 'C'. The other is that the up-down column 7 provides a rotating motion about the vertical axis which is shown in FIG. 3 as 'E', referred to as wig-wag motion.

As illustrated in FIG. 2, the cross-arm 6 is mounted on the up-down column 7. The cross-arm 6 can provide a translational motion along its length to move the G-arm forward or backward along the horizontal axis, shown in FIG. 3 as 'D'. This may be achieved in any manner, such as a slidable attachment to the up-down column 7, a telescoping or otherwise extendable cross-arm 6, or the like.

The gantry support 5 is mounted on the cross-arm 6. The gantry support 5 provides lateral motion for the G-arm imaging system. This motion is showed in FIG. 3 as 'B'.

The G-arm gantry 4 in this embodiment may be slidably mounted to the inner or outer circumference of the G-arm gantry support 5. G-arm gantry 4 with imaging chains can orbitally rotate about the gantry axis which is shown in FIG. 3 as direction A. In one embodiment, rotation may be limited by the imaging chain elements 2 $a$-$c$, 3 $a$-$c$. In another embodiment, the imaging chain elements $2a$-$c$, $3a$-$c$ may be offset to allow additional rotation of the G-arm gantry 4. Further still, in some embodiments, the imaging chain elements may be movable along the gantry 4.

As illustrated in the embodiment of FIG. 2, base 9 is composed of components 5, 6, 7 and 8. The C-arm base 9 is introduced to the G-arm equipment is an alternative embodiment in accordance with the present invention, the significance the base configuration is that more degrees of freedom of movement are provided to the G-arm X-ray imaging apparatus 1, such as the lateral motion, wig-wag motion and other motions, all of these motions (A-E) have been shown in FIG. 3. Although a mobile base 9 is taken as the example in FIG. 2, FIG. 3, FIG. 4, and FIG. 5, the present invention is not limited to such a base, indeed any type of support structure for the G-arm gantry 4 may be used. In another embodiment, a floor-mounting C-arm base or a ceiling-mounting C-arm base can be used as the G-arm base. The more degrees of freedom of movement the apparatus 1 has, the more convenient the positioning can be for both operator and patient.

Figure 4:
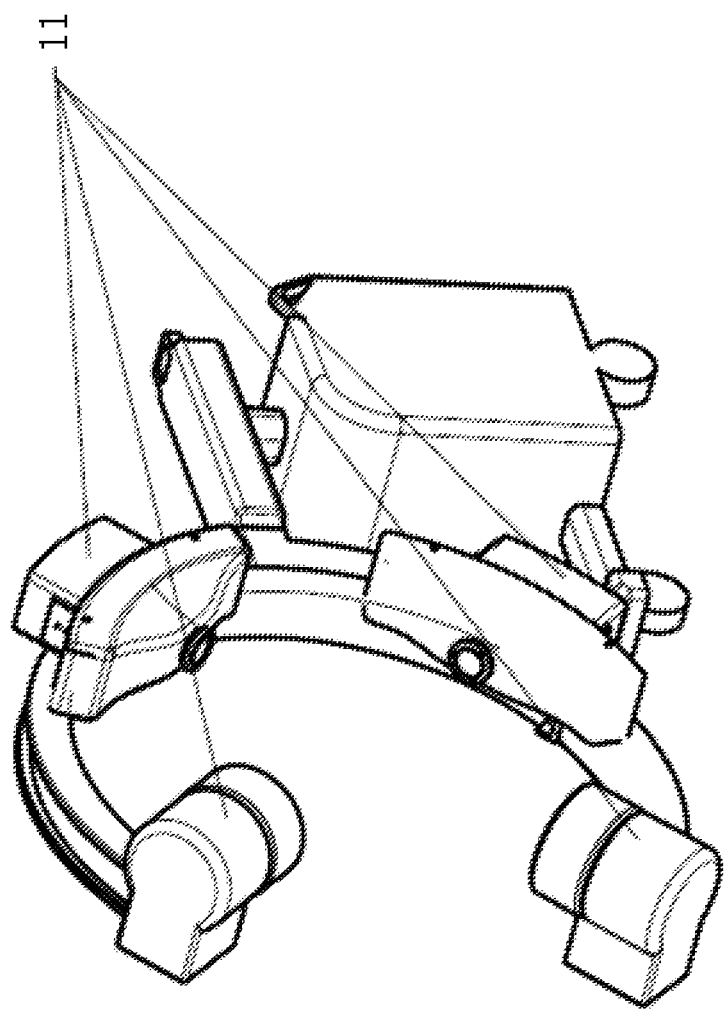
FIG. 4 provides a perspective view of another embodiment of the X-ray apparatus.
Figure 5:
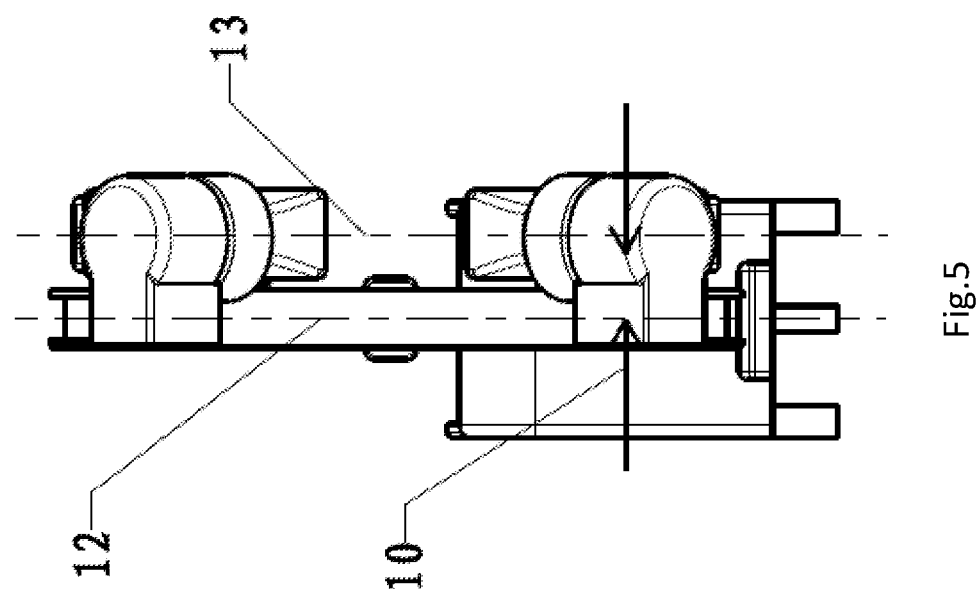
FIG. 5 indicates an embodiment of offset distance between the central plane of the image chains and the central plane of the G-arm gantry.

An alternative embodiment of the present invention is illustrated in FIG. 4 and FIG. 5. In this embodiment, two perpendicular side-mounted bi-plane G-arm imaging chains are shown. These side mounting imaging chains of the X-ray imaging machinery are shown at 11 in FIG. 4. The first set of imaging chain (receptor 2a, source 2b and collimator 2c) and the second imaging chain (receptor 3a, source 3b and collimator 3c) are both mounted on a side surface of the gantry, rather than mounted on the central plane of the G-arm gantry, 12 of FIG. 5. Also this can be explained as the central plane of the image chain, which is shown in FIG. 5 and designated as 13. The central plane 13 has an offset distance to the central plane of the G-arm gantry. The offset distance is shown in FIG. 5 and is designated as 10. A larger orbital rotation angle (direction A) is gained by the side-mounted configuration because the imaging chains are positioned out of the way. This orbital rotation angle will be larger than the existing C-arm and G-arm apparatus. This allows an operator to select a viewing angle more quickly and easily.

Figure 6:
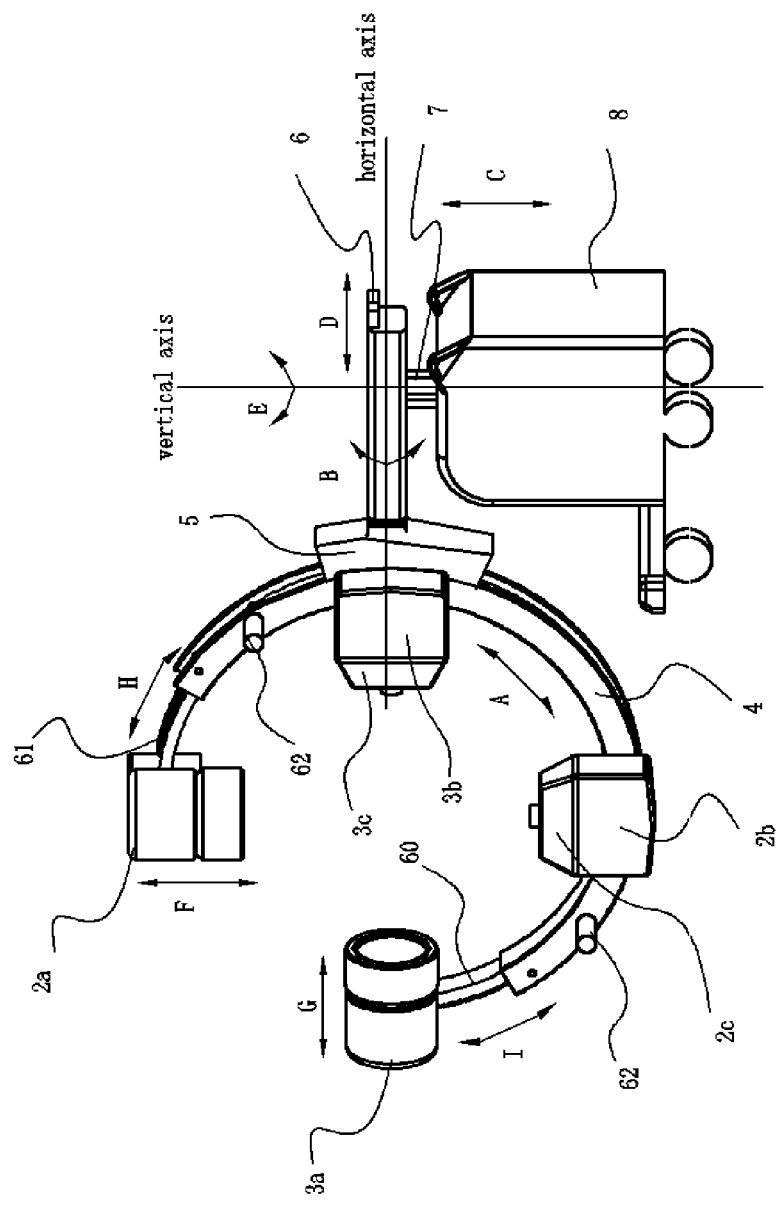
FIG. 6 provides a side view of another embodiment of the X-ray apparatus
Figure 7:
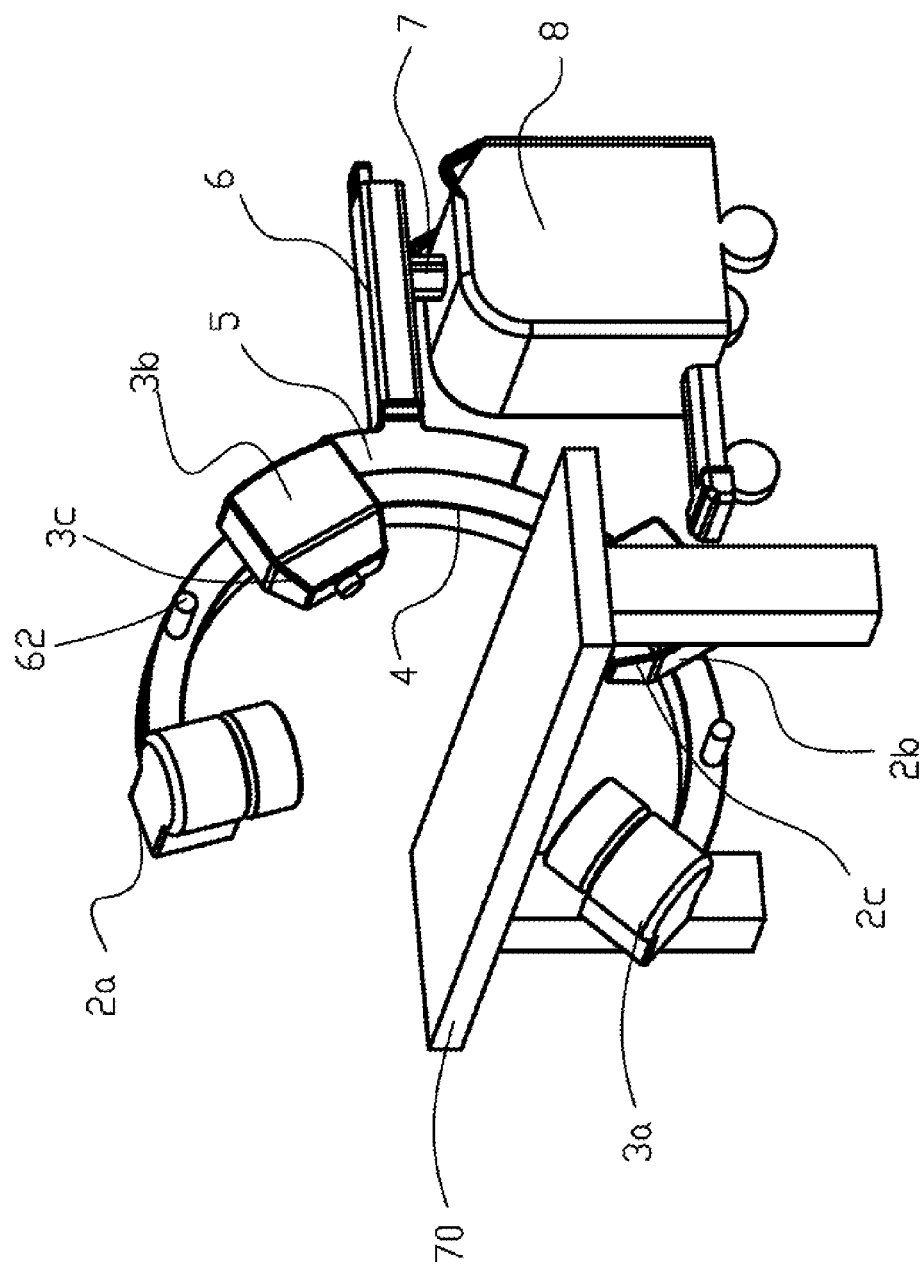
FIG. 7 provides a perspective view of yet another embodiment of the X-ray apparatus FIG. 8 provides a perspective view of still another embodiment of the X-ray apparatus
Figure 8:
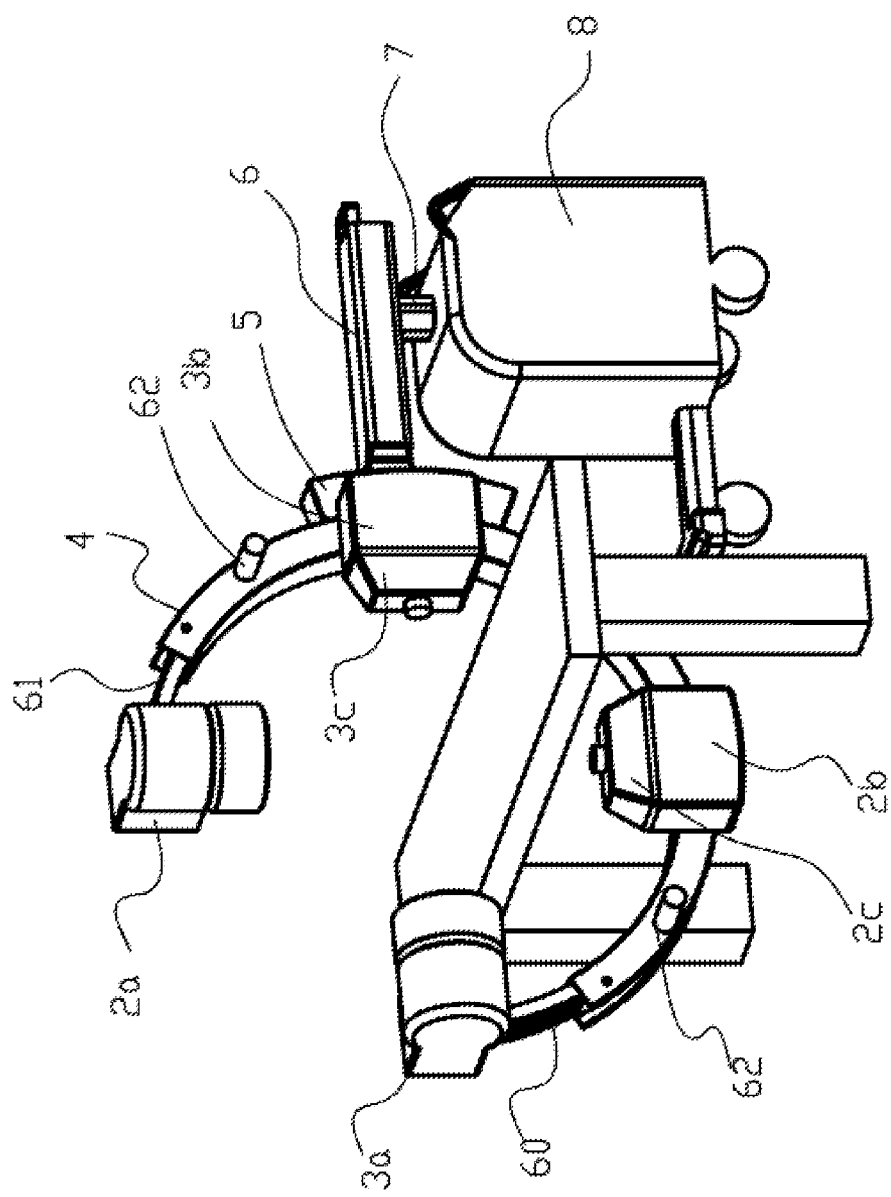

Another embodiment of the G-arm apparatus is shown in FIGS. 6 through 8. The embodiment shown has a first X-ray receptor 2a, first X-ray source 2b, first collimator 2c, second X-ray receptor 3a, second X-ray source 3b, second collimator 3c all attached to the G-arm gantry 4. The gantry support 5 connects the G-arm gantry 4 to the cross-arm 6. Further, the gantry support 5 allows the gantry to rotate with respect to the cross-arm 6 as shown by direction 'A' and 'B' of FIG. 6.

The cross-arm 6 is attached to up-down column 7. The cross-arm 6 is configured to not only support the G-arm gantry 4 but also allows a forward and back motion of the assembly as shown by direction 'D' of FIG. 6. This motion may be achieved by slideable attachment to up-down column 7, a telescoping or otherwise extendable arm 6, or the like. The up-down column 7 allows for height adjustment of the G-arm gantry 4 as well as a rotating motion about its vertical axis. These motions are represented by directions 'C' and 'E' of FIG. 6. A wheeled cart 8 supports the device and allows for its movement and orientation. The cart 8 may also provide electronics and computerized support elements required by the device, among other things.

Turning back to the G-arm gantry 4 and X-ray receptors 2a, 3a of FIGS. 6-8, it can be seen that the X-ray receptors 2a, 3a are movable along directions H and I. X-ray receptor 2a is connected to the G-arm gantry 4 via arm 61. Arm 61 is slidably mounted to the gantry and allows the X-ray receptor 2a to move between an extended position (FIGS. 6 and 8) and a retracted position (FIG. 7). Similarly, X-ray receptor 3a is connected to the G-arm gantry 4 via arm 60. In one embodiment, arms 60, 61 may be slidably mounted within the G-arm gantry 4.

In another embodiment, arms 60, 61 maybe slidably mounted to an outside surface of the G-arm gantry 4, or a track formed by the G-arm gantry 4. As such, the X-ray receptors 2a, 3a connection to the G-arm gantry 4 allows movement of X-ray receptor 2a along the path indicated by direction 'H' and movement of X-ray receptor 3a along the path indicated by direction 'I'.

In this embodiment, the first and second receptors, 2a, 3a are slidable to and from an extended and retracted position. The retracted position is shown in FIG. 7. In this retracted mode, the patient and operator may easily maneuver the device and manipulate positioning to direct the X-rays as desired. Once ready for X-ray, the receptors 2a, 3a may be extended (FIGS. 6 and 8) into position in a G-arm arrangement. Once the X-ray process is completed, the receptors 2a, 3a may again be retracted, allowing the apparatus to accommodate an operating table 70, allowing a patient to move to and from the table 70, and the like. In this embodiment, the gantry 4 has an open side and a closed side. The closed side positions the imaging chains 2a-2c, 3a-3c in a proper position over the operating table 70, while the open side of the gantry 4 allows the X-ray apparatus to be moved towards, away from the operating table 70 without adjusting the operating table 70 itself. As such, patients may remain in position on the table 70 or other similar bed, or the like, while X-ray imaging can be achieved.

A motor 62 is positioned on the G-arm gantry 4. The motor 62 may allow extension of arms 60 and/or 61. In the embodiment shown, two motors 62 are utilized, one by each arm 60, 61. In other embodiments however, a single motor may be utilized to extend and retract both arms 60, 61, or the extension and retraction may be manually achieved. In a further embodiment, motor 62, or another motor (not shown) may be utilized to achieve movement of other elements of the G-arm X-ray system along any of motions A-I.

Further still, X-ray receptors 2a, 3a are configured to be radially adjustable in directions shown at 'F' and 'G' inwardly and outwardly along a line passing through a center of the operating space of the gantry. This radial adjustment allows for an adjustment of a size of the operating space and enhances X-ray imaging and positioning. In embodiments wherein the gantry is not arc shaped, the X-ray receptors 2a, 3a may still be adjustable inwardly and outwardly in a similar manner.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

What is claimed is:

1. A bi-planar X-ray apparatus comprising:
   a support gantry;
   a first imaging chain, the first imaging chain comprising a first X-ray source, and a first X-ray receptor, the first imaging chain attached to the support gantry;
   a second imaging chain, the second imaging chain comprising a second X-ray source, and a second X-ray receptor, the second imaging chain attached to the support gantry;
   wherein the first X-ray receptor is connected to a first arm adjustably mounted to the support gantry, the first X-ray receptor movable from a retracted position to an extended operation position; and
   wherein the second X-ray receptor is connected to a second arm adjustably mounted to the support gantry, the second X-ray receptor movable from a retracted position to an extended operation position.

2. The bi-planar X-ray apparatus of claim 1 wherein the support gantry forms an arc.

3. The bi-planar X-ray apparatus of claim 2 wherein the support gantry and first and second X-ray receptors form a C-shaped arm when the X-ray receptors are in the retracted position, and form a G-shaped arm when the X-ray receptors are in the extended position.

4. The bi-planar X-ray apparatus of claim 1 wherein the gantry is attached to a gantry support, the gantry movable with respect to the gantry support to allow an orbital motion of the first and second imaging chains.

5. The bi-planar X-ray apparatus of claim 4 wherein the gantry support is attached to a cross arm, the cross arm supporting the gantry support and gantry at a proximal end, the cross arm being capable of adjustment in a direction along its length.

6. The bi-planar X-ray apparatus of claim 5 wherein the cross arm has an up-down column perpendicularly attached adjacent to a distal end, the up-down column allowing pivoting motion of the cross arm as well as allowing the cross arm to move upwardly and downwardly.

7. The bi-planar X-ray apparatus of claim 6 wherein the up-down column is attached to a wheeled cart.

8. The bi-planar X-ray apparatus of claim 1 further comprising a motor to move at least one of the first and second X-ray receptors between the extended position and the retracted position.

9. The bi-planar X-ray apparatus of claim 1 wherein the first imaging chain and second imaging chain are arranged to perpendicularly.

10. The bi-planar X-ray apparatus of claim 1 wherein the first arm is slidable within the gantry.

11. The bi-planar X-ray apparatus of claim 1 wherein the first arm is slidable along an external edge of the gantry.

12. The bi-planar X-ray apparatus of claim 1 wherein the first and second imaging chains are attached to a side surface of the gantry.

13. The bi-planar X-ray apparatus of claim 1 wherein the first and second imaging chains are attached along a central plane of the gantry.

14. The bi-planar X-ray apparatus of claim 2 wherein the first X-ray receptor is adjustable in a radial direction of the arc shaped gantry.

15. The bi-planar X-ray apparatus of claim 14 wherein the second X-ray receptor is adjustable in the radial direction of the arc shaped gantry.

16. The bi-planar X-ray apparatus of claim 1 further comprising a computerized control system, the computerized control system in communication with the first and second imaging chains and capable of controlling operation of each of the first and second imaging chains.

17. The bi-planar X-ray apparatus of claim 16 wherein the computerized control system is configured to allow simultaneous operation of the first and second imaging chains.

18. The bi-planar X-ray apparatus of claim 16 wherein the computerized control system is configured to allow operation of one of the first and second imaging chains at a time.

19. The bi-planar X-ray apparatus of claim 1 further comprising a display capable of displaying an image produced by one of the first imaging chain and the second imaging chain.

20. A bi-planar X-ray apparatus comprising:

a support gantry the support gantry having an arced shape, the arced shape having a closed side and an open side;

a first imaging chain, the first imaging chain comprising a first X-ray source, and a first X-ray receptor, the first imaging chain attached to the support gantry;

a second imaging chain, the second imaging chain comprising a second X-ray source, and a second X-ray receptor, the second imaging chain attached to the support gantry;

wherein the first X-ray receptor is connected to a first arm adjustably mounted to the support gantry, the first X-ray receptor movable from a retracted position to an extended operation position;

wherein the second X-ray receptor is connected to a second arm adjustably mounted to the support gantry, the second X-ray receptor movable from a retracted position to an extended operation position; and an operation table, the gantry positioned such that the closed side extends under the operation table and over the operation table, the table movable away from the gantry through the open side.

\* \* \* \* \*